US006461994B1

(12) United States Patent
Gibson et al.

(10) Patent No.: US 6,461,994 B1
(45) Date of Patent: Oct. 8, 2002

(54) POLYMERIZATION CATALYST

(75) Inventors: Vernon Charles Gibson, London; Brian Stephen Kimberley, Sunbury on Thames; Peter James Maddox, Staines, all of (GB); Sergio Mastroianni, Martigues (FR)

(73) Assignee: BP Chemicals Limited, London (GB)

( * ) Notice: Subject to any disclaimer, the term of this patent is extended or adjusted under 35 U.S.C. 154(b) by 0 days.

(21) Appl. No.: 09/674,378

(22) Filed: Oct. 30, 2000

Related U.S. Application Data

(63) Continuation of application No. PCT/GB99/02888, filed on Sep. 1, 1999.

(30) Foreign Application Priority Data

Sep. 12, 1998 (GB) .............................................. 9819847

(51) Int. Cl.⁷ .............................. B01J 31/18; C08F 4/44
(52) U.S. Cl. ....................... 502/155; 502/167; 526/64; 526/75; 526/115; 526/116; 526/161; 526/171; 526/172; 526/901; 526/905
(58) Field of Search ........................ 526/172, 64, 75, 526/115, 116, 905, 901, 161, 121; 502/155, 167; 556/138

(56) References Cited

U.S. PATENT DOCUMENTS 5,955,555 * 9/1999 Bennett ...................... 526/133

FOREIGN PATENT DOCUMENTS

| WO | WO 98/27124 | 6/1998 |
| WO | WO 98/30612 | 7/1998 |
| WO | WO 99/12981 | 3/1999 |

OTHER PUBLICATIONS

B. çetinkaya et al., "Ruthenium (II) Complexes with 2,6–Pyridyl–Diimine Ligands: Synthesis, Characterization and Catalytic Activity in Epoxidation Reactions", Journal of Molecular Catalysis A: Chemical, vol. 142, pp. 101–112, (1999).

M.J. Blandamer et al., "Solubilities of Salts and Kinetics of Reaction between Hydroxide Ions and Iron (II)–Di–imine Complexes in Water–Methanol Mixtures", J. Chem. Soc., Faraday Trans. 1, vol. 82, pp. 1471–1514, (1986).

* cited by examiner

Primary Examiner—David W. Wu
Assistant Examiner—R. Harlan
(74) Attorney, Agent, or Firm—Finnegan, Henderson, Farabow, Garrett and Dunner, L.L.P.

(57) ABSTRACT

The present invention relates to transition metal complex compounds, to polymerization catalysts based thereon and to their use in the polymerization and copolymerization of olefins.

33 Claims, No Drawings

POLYMERIZATION CATALYST

RELATED APPLICATION

This application is a Continuation of International Application Number PCT/GB99/02888, filed Sep. 1, 1999.

The present invention relates to transition metal complex compounds, to polymerisation catalysts based thereon and to their use in the polymerisation and copolymerisation of olefins.

The use of certain transition metal compounds to polymerise 1-olefins, for example, ethylene or propylene, is well established in the prior art. The use of Ziegler-Natta catalysts, for example, those catalysts produced by activating titanium halides with organometallic compounds such as triethylaluminium, is fundamental to many commercial processes for manufacturing polyolefins. Over the last twenty or thirty years, advances in the technology have led to the development of Ziegler-Natta catalysts which have such high activities that olefin polymers and copolymers containing very low concentrations of residual catalyst can be produced directly in commercial polymerisation processes. The quantities of residual catalyst remaining in the produced polymer are so small as to render unnecessary their separation and removal for most commercial applications. Such processes can be operated by polymerising the monomers in the gas phase, or in solution or in suspension in a liquid hydrocarbon diluent. Polymerisation of the monomers can be carried out in the gas phase (the "gas phase process"), for example by fluidising under polymerisation conditions a bed comprising the target polyolefin powder and particles of the desired catalyst using a fluidising gas stream comprising the gaseous monomer. In the so-called "solution process" the (co)polymerisation is conducted by introducing the monomer into a solution or suspension of the catalyst in a liquid hydrocarbon diluent under conditions of temperature and pressure such that the produced polyolefin forms as a solution in the hydrocarbon diluent. In the "slurry process" the temperature, pressure and choice of diluent are such that the produced polymer forms as a suspension in the liquid hydrocarbon diluent. These processes are generally operated at relatively low pressures (for example 10–50 bar) and low temperature (for example 50 to 150° C.).

In recent years the use of certain metallocene catalysts (for example biscyclopentadienylzirconiumdichloride activated with alumoxane) has provided catalysts with potentially high activity. However, metallocene catalysts of this type suffer from a number of disadvantages, for example, high sensitivity to impurities when used with commercially available monomers, diluents and process gas streams, the need to use large quantities of expensive alumoxanes to achieve high activity, and difficulties in putting the catalyst on to a suitable support.

WO 99/12981 discloses that ethylene and other 1-olefins may be polymerised by contacting it with certain late transition metal complexes of selected 2,6-pyridinecarboxaldehydebis (imines) and 2,6-diacylpyridinebis (imines).

An object of the present invention is to provide a novel catalyst suitable for polymerising and oligomerising monomers, for example, olefins such as α-olefins containing from 2 to 20 carbon atoms, and especially for polymerising ethylene alone, propylene alone, or for copolymerising ethylene or propylene with other 1-olefins such as $C_{2-20}$ α-olefins. A further object of the invention is to provide an improved process for the polymerisation of olefins, especially of ethylene alone or the copolymerisation of ethylene or propylene with higher 1-olefins to provide homopolymers and copolymers having controllable molecular weights. For example, using the catalysts of the present invention there can be made a wide variety of products such as, for example, liquid polyolefins, oligomers, linear α-olefins, branched α-olefins, resinous or tacky polyolefins, solid polyolefins suitable for making flexible film and solid polyolefins having high stiffness.

SUMMARY OF THE INVENTION

The present invention provides a nitrogen containing transition metal complex having the following Formula (I)

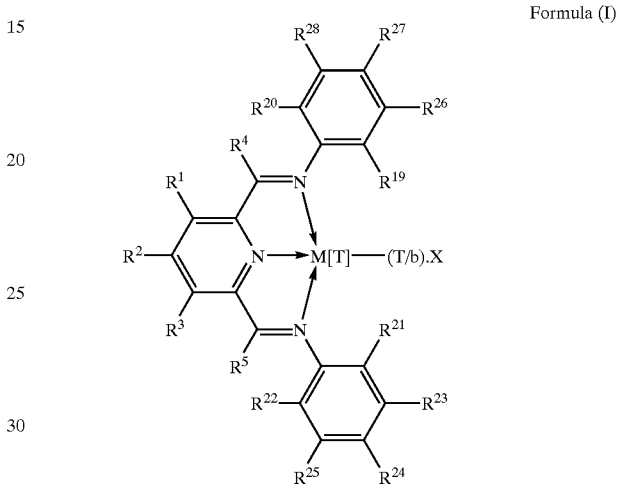

Formula (I)

wherein M is Fe[II], Fe[III], Co[I], Co[II], Co[III], Mn[I], Mn[II], Mn[III], Mn[IV], Ru[II], Ru[III] or Ru[IV]; X represents an atom or group covalently or ionically bonded to the transition metal M; T is the oxidation state of the transition metal M and b is the valency of the atom or group X; $R^1$, $R^2$, $R^3$, $R^4$, $R^5$, $R^{19}$, $R^{20}$, $R^{21}$, $R^{22}$, $R^{23}$, $R^{25}$, $R^{26}$ and $R^{28}$ are independently selected from hydrogen, halogen, hydrocarbyl, substituted hydrocarbyl, heterohydrocarbyl or substituted heterohydrocarbyl; when any two or more of $R^1$ $R^2$, $R^3$, $R^4$ and $R^5$ and are hydrocarbyl, substituted hydrocarbyl, heterohydrocarbyl or substituted heterohydrocarbyl, said two or more can be linked to form one or more cyclic substituents;

characterised in that $R^{24}$ and $R^{27}$ are either both halogen or at least one of them has two or more carbon atoms.

DETAILED DESCRIPTION OF THE INVENTION $R^1$, $R^2$, $R^3$, $R^4$, $R^5$, $R^{19}$, $R^{20}$, $R^{21}$, $R^{22}$, $R^{23}$, $R^{25}$, $R^{26}$ and $R^{28}$ are preferably independently selected from hydrogen and $C_1$ to $C_8$ hydrocarbyl, for example, methyl, ethyl, n-propyl, n-butyl, n-hexyl, n-octyl, phenyl and benzyl.

When $R^{24}$ and $R^{27}$ are both halogen, they may independently be fluorine, chlorine, bromine or iodine, and are preferably both fluorine.

In the case where at least one of $R^{24}$ and $R^{27}$ contains two carbon atoms, they preferably have from 2 to 10 carbon atoms, more preferably from 4 to 8 carbon atoms. If desired one, but not both, of the groups $R^{24}$ and $R^{27}$ can be selected from hydrogen or methyl. However, it is preferred that both $R^{24}$ and $R^{27}$ contain from 2 to 10 carbon atoms, most preferably from 4 to 8 carbon atoms. $R^{24}$ and $R^{27}$ are preferably independently selected from ethyl, n-propyl, iso-propyl, n-butyl, sec-butyl, tert.-butyl, n-pentyl, neopentyl, n-hexyl, 4-methylpentyl, n-octyl, phenyl and benzyl. Most preferably in this case $R^{24}$ and $R^{27}$ are both tertiary butyl.

Alternatively, one of $R^{24}$ and $R^{27}$ contains at least two carbon atoms and the other is halogen, preferably fluoro.

Preferably at least one of $R^{19}$, $R^{20}$, $R^{21}$ and $R^{22}$ is hydrocarbyl, substituted hydrocarbyl, heterohydrocarbyl or substituted heterohydrocarbyl. More preferably at least one of $R^{19}$ and $R^{20}$, and at least one of $R^{21}$ and $R^{22}$, is hydrocarbyl, substituted hydrocarbyl, heterohydrocarbyl or substituted heterohydrocarbyl. Most preferably $R^{19}$, $R^{20}$, $R^{21}$ and $R^{22}$ are all independently selected from hydrocarbyl, substituted hydrocarbyl, heterohydrocarbyl or substituted heterohydrocarbyl. $R^{19}$, $R^{20}$, $R^{21}$ and $R^{22}$ are preferably independently selected from methyl, ethyl, n-propyl, iso-propyl, n-butyl, sec-butyl, tert.-butyl, n-pentyl, neopentyl, n-hexyl, 4-methylpentyl, n-octyl, phenyl and benzyl. However in the case when $R^{24}$ and $R^{27}$ are both halogen, it is preferred that one of $R^{21}$ and $R^{22}$ and also one of $R^{19}$ and $R^{20}$ is hydrogen.

Preferably $R^{23}$, $R^{25}$, $R^{26}$ and $R^{28}$ are all hydrogen.

In the nitrogen-containing complex of the present invention the transition metal M is preferably Fe(II), Fe(III) or Co(II).

Each of the nitrogen atoms $N^1$, $N^2$ and $N^3$ is coordinated to the transition metal M by a "dative" bond, ie a bond formed by donation of a lone pair of electrons from the nitrogen atom. The remaining bonds on each nitrogen atom are covalent bonds formed by electron sharing between the nitrogen atoms and the organic ligand as shown in the defined formula for the transition metal complex illustrated above.

The atom or group represented by X in the compounds of Formula (I) can be, for example, selected from halide, sulphate, nitrate, thiolate, thiocarboxylate, $BF_4^-$; $PF_6^-$, hydride, hydrocarbyloxide, carboxylate, hydrocarbyl, substituted hydrocarbyl and heterohydrocarbyl, or β-diketonates. Examples of such atoms or groups are chloride, bromide, methyl, ethyl, propyl, butyl, octyl, decyl, phenyl, benzyl, methoxide, ethoxide, isopropoxide, tosylate, triflate, fomate, acetate, phenoxide and benzoate. Preferred examples of the atom or group X in the compounds of Formula (I) are halide, for example, chloride, bromide; hydride; hydrocarbyloxide, for example, methoxide, ethoxide, isopropoxide, phenoxide; carboxylate, for example, formate, acetate, benzoate; hydrocarbyl, for example, methyl, ethyl, propyl, butyl, octyl, decyl, phenyl, benzyl; substituted hydrocarbyl; heterohydrocarbyl; tosylate; and triflate. Preferably X is selected from halide, hydride and hydrocarbyl. Chloride is particularly preferred.

Examples of complexes of the present invention include 2,6-diacetylpyridinebis(2,6 dimethyl 4, t-butyl anil)$FeCl_2$, 2,6-diacetylpyridinebis(2,6 dimethyl 4, t-butyl anil)$CoCl_2$, 2,6-diacetylpyridinebis(2,6 dimethyl 4, t-butyl anil)$FeBr_2$, 2,6-diacetylpyridinebis(4, t-butyl anil)$FeCl_2$, and 2,6-diacetylpyridinebis(2,6-dimethyl 4-phenyl anil)$FeCl_2$ and 2,6-diacetylpyridinebis(2-methyl, 4-fluoroanil)$FeCl_2$.

The present invention further provides a polymerisation catalyst comprising (1) a compound having the Formula (I) as hereinbefore defined, and (2) an activating quantity of at least one activator compound.

The activator compound for the catalyst of the present invention is suitably selected from organoaluminium compounds and hydrocarbylboron compounds. Suitable organoaluminium compounds include compounds of the formula $AlR_3$, where each R is independently $C_1$–$C_{12}$ alkyl or halo. Examples include trimethylaluminium (TMA), triethylaluminium (TEA), tri-isobutylaluminium (TIBA), tri-n-octylaluminium, methylaluminium dichloride, ethylaluminium dichloride, dimethylaluminium chloride, diethylaluminium chloride, ethylaluminiumsesquichloride, methylaluminiumsesquichloride, and alumoxanes. Alumoxanes are well known in the art as typically the oligomeric compounds which can be prepared by the controlled addition of water to an allylaluminium compound, for example trimethylaluminium. Such compounds can be linear, cyclic or mixtures thereof. Commercially available alumoxanes are generally believed to be mixtures of linear and cyclic compounds. The cyclic alumoxanes can be represented by the formula $[R^{16}AlO]_s$ and the linear alumoxanes by the formula $R^{17}(R^{18}AlO)_s$ wherein s is a number from about 2 to 50, and wherein $R^{16}$, $R^{17}$, and $R^{18}$ represent hydrocarbyl groups, preferably $C_1$ to $C_6$ alkyl groups, for example methyl, ethyl or butyl groups. Alkylalumoxanes such as methylalumoxane (MAO) are preferred.

Mixtures of alkylalumoxanes and trialkylaluminium compounds are particularly preferred, such as MAO with TMA or TIBA. In this context it should be noted that the term "alkylalumoxane" as used in this specification includes alkylalumoxanes available commercially which may contain a proportion, typically about 10 wt %, but optionally up to 50 wt %, of the corresponding trialkylaluminium; for instance, commercial MAO usually contains approximately 10 wt % trimethylaluminium (TMA), whilst commercial MMAO contains both TMA and TIBA. Quantities of alkylalumoxane quoted herein include such trialkylaluminium impurities, and accordingly quantities of trialkylaluminium compounds quoted herein are considered to comprise compounds of the formula $AlR^3$ additional to any $AlR_3$ compound incorporated within the alkylalumoxane when present.

Examples of suitable hydrocarbylboron compounds are boroxines, trimethylboron, triethylboron, dimethylphenylammoniumtetra(phenyl)borate, trityltetra(phenyl)borate, triphenylboron, dimethylphenylammonium tetra(pentafluorophenyl)borate, sodium tetrakis[(bis-3,5-trifluoromethyl)phenyl]borate, $H^+(OEt_2)[(bis-3,5-trifluoromethyl)phenyl]borate$, trityltetra(pentafluorophenyl)borate and tris(pentafluorophenyl)boron.

In the preparation of the catalysts of the present invention the quantity of activating compound selected from organoaluminium compounds and hydrocarbylboron compounds to be employed is easily determined by simple testing, for example, by the preparation of small test samples which can be used to polymerise small quantities of the monomer(s) and thus to determine the activity of the produced catalyst. It is generally found that the quantity employed is sufficient to provide 0.1 to 20,000 atoms, preferably 1 to 2000 atoms of aluminium or boron per atom of metal M in the compound of Formula (I).

An alternative class of activators comprise salts of a cationic oxidising agent and a non-coordinating compatible anion. Examples of cationic oxidising agents include: ferrocenium, hydrocarbyl-substituted ferrocenium, $Ag^+$, or $Pb^{2+}$. Examples of non-coordinating compatible anions are $BF_4^-$, $SbCl_6^-$, $PF_6^-$; tetrakis(phenyl)borate and tetrakis (pentafluorophenyl)borate.

A further aspect of the present invention provides a polymerisation catalyst system comprising (1) a compound having the Formula (I) as hereinbefore defined, including all the compounds excluded above, (2) an activating quantity of at least one activator compound as defined above, and (3) a neutral Lewis base.

Neutral Lewis bases are well known in the art of Ziegler-Natta catalyst polymerisation technology. Examples of classes of neutral Lewis bases suitably employed in the present invention are unsaturated hydrocarbons, for example, alkenes (other than 1-olefins) or alkynes, primary, secondary and tertiary amines, amides, phosphoramides, phosphines, phosphites, ethers, thioethers, nitriles, carbonyl compounds, for example, esters, ketones, aldehydes, carbon monoxide and carbon dioxide, sulphoxides, sulphones and boroxines. Although 1-olefins are capable of acting as neutral Lewis bases, for the purposes of the present invention they are regarded as monomer or comonomer 1-olefins and not as neutral Lewis bases per se. However, alkenes which are internal olefins, for example, 2-butene and cyclohexene are regarded as neutral Lewis bases in the present invention. Preferred Lewis bases are tertiary amines and aromatic esters, for example, dimethylaniline, diethylaniline, tributylamine, ethylbenzoate and benzylbenzoate. In this particular aspect of the present invention, components (1), (2) and (3) of the catalyst system can be brought together simultaneously or in any desired order. However, if components (2) and (3) are compounds which interact together strongly, for example, form a stable compound together, it is preferred to bring together either components (1) and (2) or components (1) and (3) in an initial step before introducing the final defined component. Preferably components (1) and (3) are contacted together before component (2) is introduced. The quantities of components (1) and (2) employed in the preparation of this catalyst system are suitably as described above in relation to the catalysts of the present invention. The quantity of the neutral Lewis Base [component (3)] is preferably such as to provide a ratio of component (1):component (3) in the range 100:1 to 1:1000, most preferably in the range 1:1 to 1:20. Components (1), (2) and (3) of the catalyst system can brought together, for example, as the neat materials, as a suspension or solution of the materials in a suitable diluent or solvent (for example a liquid hydrocarbon), or, if at least one of the components is volatile, by utilising the vapour of that component. The components can be brought together at any desired temperature. Mixing the components together at room temperature is generally satisfactory. Heating to higher temperatures e.g. up to 120° C. can be carried out if desired, e.g. to achieve better mixing of the components. It is preferred to carry out the bringing together of components (1), (2) and (3) in an inert atmosphere (e.g. dry nitrogen) or in vacuo. If it is desired to use the catalyst on a support material (see below), this can be achieved, for example, by preforming the catalyst system comprising components (1), (2) and (3) and impregnating the support material preferably with a solution thereof, or by introducing to the support material one or more of the components simultaneously or sequentially. If desired the support material itself can have the properties of a neutral Lewis base and can be employed as, or in place of, component (3). An example of a support material having neutral Lewis base properties is poly(aminostyrene) or a copolymer of styrene and aminostyrene (ie vinylaniline).

The catalysts of the present invention can if desired comprise more than one of the defined compounds. Alternatively, the catalysts of the present invention can also include one or more other types of transition metal compounds or catalysts, for example, nitrogen containing catalysts such as those described in our copending applications PCT/GB98102638 or GB 9903402.7. Examples of such other catalysts include 2,6-diacetylpyridinebis(2,4,6-trimethyl anil)FeCl$_2$.

The catalysts of the present invention can also include one or more other types of catalyst, such as those of the type used in conventional Ziegler-Natta catalyst systems, metallocene-based catalysts, monocyclopentadienyl- or constrained geometry based catalysts, or heat activated supported chromium oxide catalysts (eg Phillips-type catalyst).

The catalysts of the present invention can be unsupported or supported on a support material, for example, silica, alumina, MgCl$_2$ or zirconia, or on a polymer or prepolymer, for example polyethylene, polypropylene, polystyrene, or poly(aminostyrene).

If desired the catalysts can be formed in situ in the presence of the support material, or the support material can be pre-impregnated or premixed, simultaneously or sequentially, with one or more of the catalyst components. The catalysts of the present invention can if desired be supported on a heterogeneous catalyst, for example, a magnesium halide supported Ziegler Natta catalyst, a Phillips type (chromium oxide) supported catalyst or a supported metallocene catalyst. Formation of the supported catalyst can be achieved for example by treating the transition metal compounds of the present invention with alumoxane in a suitable inert diluent, for example a volatile hydrocarbon, slurrying a particulate support material with the product and evaporating the volatile diluent. The produced supported catalyst is preferably in the form of a free-flowing powder. The quantity of support material employed can vary widely, for example from 100,000 to 1 grams per gram of metal present in the transition metal compound.

The present invention further provides a process for the polymerisation and copolymerisation of 1-olefins, comprising contacting the monomeric olefin under polymerisation conditions with the polymerisation catalyst or catalyst system of the present invention. A preferred process comprises the steps of:

a) preparing a prepolymer-based catalyst by contacting one or more 1-olefins with a catalyst system, and b) contacting the prepolymer-based catalyst with one or more 1-olefins, wherein the catalyst system is as defined above.

The present invention also encompasses as another aspect the use of a complex as defined above as a catalyst for the polymerisation of 1-olefins.

In the text hereinbelow, the term "catalyst" is intended to include "catalyst system" as defined previously and also "prepolymer-based catalyst" as defined above.

The polymerisation conditions can be, for example, solution phase, slurry phase, gas phase or bulk phase, with polymerisation temperatures ranging from −100° C. to +300° C., and at pressures of atmospheric and above, particularly from 140 to 4100 kPa. If desired, the catalyst can be used to polymerise ethylene under high pressure/high temperature process conditions wherein the polymeric material forms as a melt in supercritical ethylene. Preferably the polymerisation is conducted under gas phase fluidised bed or stirred bed conditions.

Suitable monomers for use in the polymerisation process of the present invention are, for example, ethylene and: $C_{2-20}$ α-olefins, specifically propylene, 1-butene, 1-pentene, 1-hexene, 4-methylpentene-1, 1-heptene, 1-octene, 1-nonene, 1-decene, 1-undecene, 1-dodecene, 1-tridecene, 1-tetradecene, 1-pentadecene, 1-hexadecene, 1-heptadecene, 1-octadecene, 1-nonadecene, and 1-eicosene. Other monomers include methyl methacrylate, methyl acrylate, butyl acrylate, acrylonitrile, vinyl acetate, and styrene. Preferred monomers for homopolymerisation processes are ethylene and propylene.

The catalysts and process of the invention can also be used for copolymerising ethylene or propylene with each other or with other 1-olefins such as 1-butene, 1-hexene, 4-methylpentene-1, and octene, or with other monomeric materials, for example, methyl methacrylate, methyl acrylate, butyl acrylate, acrylonitrile, vinyl acetate, and styrene.

Irrespective of the polymerisation or copolymerisation technique employed, polymerisation or copolymerisation is typically carried out under conditions that substantially exclude oxygen, water, and other materials that act as catalyst poisons. Also, polymerisation or copolymerisation can be carried out in the presence of additives to control polymer or copolymer molecular weights.

The use of hydrogen gas as a means of controlling the average molecular weight of the polymer or copolymer applies generally to the polymerisation process of the present invention. For example, hydrogen can be used to reduce the average molecular weight of polymers or copolymers prepared using gas phase, slurry phase, bulk phase or solution phase polymerisation conditions. The quantity of hydrogen gas to be employed to give the desired average molecular weight can be determined by simple "trial and error" polymerisation tests.

The polymerisation process of the present invention provides polymers and copolymers, especially ethylene polymers, at remarkably high productivity (based on the amount of polymer or copolymer produced per unit weight of complex employed in the catalyst system). This means that relatively very small quantities of transition metal complex are consumed in commercial processes using the process of the present invention. It also means that when the polymerisation process of the present invention is operated under polymer recovery conditions that do not employ a catalyst separation step, thus leaving the catalyst, or residues thereof, in the polymer (e.g. as occurs in most commercial slurry and gas phase polymerisation processes), the amount of transition metal complex in the produced polymer can be very small.

Slurry phase polymerisation conditions or gas phase polymerisation conditions are particularly useful for the production of high or low density grades of polyethylene, and polypropylene. In these processes the polymerisation conditions can be batch, continuous or semi-continuous. Furthermore, one or more reactors may be used, e.g. from two to five reactors in series. Different reaction conditions, such as different temperatures or hydrogen concentrations may be employed in the different reactors. In the slurry phase process and the gas phase process, the catalyst is generally metered and transferred into the polymerisation zone in the form of a particulate solid either as a dry powder (e.g. with an inert gas) or as a slurry. This solid can be, for example, a solid catalyst system formed from the one or more of complexes of the invention and an activator with or without other types of catalysts, or can be the solid catalyst alone with or without other types of catalysts. In the latter situation, the activator can be fed to the polymerisation zone, for example as a solution, separately from or together with the solid catalyst. Preferably the catalyst system or the transition metal complex component of the catalyst system employed in the slurry polymerisation and gas phase polymerisation is supported on one or more support materials. Most preferably the catalyst system is supported on the support material prior to its introduction into the polymerisation zone. Suitable support materials are, for example, silica, alumina, zirconia, talc, kieselguhr, or magnesia. Impregnation of the support material can be carried out by conventional techniques, for example, by forming a solution or suspension of the catalyst components in a suitable diluent or solvent, and slurrying the support material therewith. The support material thus impregnated with catalyst can then be separated from the diluent for example, by filtration or evaporation techniques. Once the polymer product is discharged from the reactor, any associated and absorbed hydrocarbons are substantially removed, or degassed, from the polymer by, for example, pressure let-down or gas purging using fresh or recycled steam, nitrogen or light hydrocarbons (such as ethylene). Recovered gaseous or liquid hydrocarbons may be recycled to the polymerisation zone.

In the slurry phase polymerisation process the solid particles of catalyst, or supported catalyst, are fed to a polymerisation zone either as dry powder or as a slurry in the polymerisation diluent. The polymerisation diluent is compatible with the polymer(s) and catalyst(s), and may be an alkane such as hexane, heptane, isobutane, or a mixture of hydrocarbons or paraffins. Preferably the particles are fed to a polymerisation zone as a suspension in the polymerisation diluent. The polymerisation zone can be, for example, an autoclave or similar reaction vessel, or a continuous loop reactor, e.g. of the type well-know in the manufacture of polyethylene by the Phillips Process. When the polymerisation process of the present invention is carried out under slurry conditions the polymerisation is preferably carried out at a temperature above 0° C., most preferably above 15° C. The polymerisation temperature is preferably maintained below the temperature at which the polymer commences to soften or sinter in the presence of the polymerisation diluent. If the temperature is allowed to go above the latter temperature, fouling of the reactor can occur. Adjustment of the polymerisation within these defined temperature ranges can provide a useful means of controlling the average molecular weight of the produced polymer. A further useful means of controlling the molecular weight is to conduct the polymerisation in the presence of hydrogen gas which acts as chain transfer agent. Generally, the higher the concentration of hydrogen employed, the lower the average molecular weight of the produced polymer.

In bulk polymerisation processes, liquid monomer such as propylene is used as the polymerisation medium.

Methods for operating gas phase polymerisation processes are well known in the art. Such methods generally involve agitating (e.g. by stirring, vibrating or fluidising) a bed of catalyst, or a bed of the target polymer (i.e. polymer having the same or similar physical properties to that which it is desired to make in the polymerisation process) containing a catalyst, and feeding thereto a stream of monomer at least partially in the gaseous phase, under conditions such that at least part of the monomer polymerises in contact with the catalyst in the bed. The bed is generally cooled by the addition of cool gas (e.g. recycled gaseous monomer) and/or volatile liquid (e.g. a volatile inert hydrocarbon, or gaseous monomer which has been condensed to form a liquid). The polymer produced in, and isolated from, gas phase processes forms directly a solid in the polymerisation zone and is free from, or substantially free from liquid. As is well known to those skilled in the art, if any liquid is allowed to enter the polymerisation zone of a gas phase polymerisation process the quantity of liquid in the polymerisation zone is small in relation to the quantity of polymer present. This is in contrast to "solution phase" processes wherein the polymer is formed dissolved in a solvent, and "slurry phase" processes wherein the polymer forms as a suspension in a liquid diluent.

The gas phase process can be operated under batch, semi-batch, or so-called "continuous" conditions. It is preferred to operate under conditions such that monomer is continuously recycled to an agitated polymerisation zone containing polymerisation catalyst, make-up monomer being provided to replace polymerised monomer, and continuously or intermittently withdrawing produced polymer from the polymerisation zone at a rate comparable to the rate of formation of the polymer, fresh catalyst being added to the polymerisation zone to replace the catalyst withdrawn form the polymerisation zone with the produced polymer.

For typical production of impact copolymers, homopolymer formed from the first monomer in a first reactor is reacted with the second monomer in a second reactor. For manufacture of propylene/ethylene impact copolymer in a gas-phase process, propylene is polymerized in a first reactor; reactive polymer transferred to a second reactor in which ethylene or other comonomer is added. The result is an intimate mixture of a isotactic polypropylene chains with chains of a random propylene/ethylene copolymer. A random copolymer typically is produced in a single reactor in which a minor amount of a comonomer (typically ethylene) is added to polymerizing chains of propylene.

Methods for operating gas phase fluidised bed processes for making polyethylene, ethylene copolymers and polypropylene are well known in the art. The process can be operated, for example, in a vertical cylindrical reactor equipped with a perforated distribution plate to support the bed and to distribute the incoming fluidising gas stream through the bed. The fluidising gas circulating through the bed serves to remove the heat of polymerisation from the bed and to supply monomer for polymerisation in the bed. Thus the fluidising gas generally comprises the monomer(s) normally together with some inert gas (e.g. nitrogen or inert hydrocarbons such as methane, ethane, propane, butane, pentane or hexane) and optionally with hydrogen as molecular weight modifier. The hot fluidising gas emerging from the top of the bed is led optionally through a velocity reduction zone (this can be a cylindrical portion of the reactor having a wider diameter) and, if desired, a cyclone and or filters to disentrain fine solid particles from the gas stream. The hot gas is then led to a heat exchanger to remove at least part of the heat of polymerisation. Catalyst is preferably fed continuously or at regular intervals to the bed. At start up of the process, the bed comprises fluidisable polymer which is preferably similar to the target polymer. Polymer is produced continuously within the bed by the polymerisation of the monomer(s). Preferably means are provided to discharge polymer from the bed continuously or at regular intervals to maintain the fluidised bed at the desired height. The process is generally operated at relatively low pressure, for example, at 10 to 50 bars, and at temperatures for example, between 50 and 120° C. The temperature of the bed is maintained below the sintering temperature of the fluidised polymer to avoid problems of agglomeration.

In the gas phase fluidised bed process for polymerisation of olefins the heat evolved by the exothermic polymerisation reaction is normally removed from the polymerisation zone (i.e. the fluidised bed) by means of the fluidising gas stream as described above. The hot reactor gas emerging from the top of the bed is led through one or more heat exchangers wherein the gas is cooled. The cooled reactor gas, together with any make-up gas, is then recycled to the base of the bed. In the gas phase fluidised bed polymerisation process of the present invention it is desirable to provide additional cooling of the bed (and thereby improve the space time yield of the process) by feeding a volatile liquid to the bed under conditions such that the liquid evaporates in the bed thereby absorbing additional heat of polymerisation from the bed by the "latent heat of evaporation" effect. When the hot recycle gas from the bed enters the heat exchanger, the volatile liquid can condense out. In one embodiment of the present invention the volatile liquid is separated from the recycle gas and reintroduced separately into the bed. Thus, for example, the volatile liquid can be separated and sprayed into the bed. In another embodiment of the present invention the volatile liquid is recycled to the bed with the recycle gas. Thus the volatile liquid can be condensed from the fluidising gas stream emerging from the reactor and can be recycled to the bed with recycle gas, or can be separated from the recycle gas and then returned to the bed.

The method of condensing liquid in the recycle gas stream and returning the mixture of gas and entrained liquid to the bed is described in EP-A-0089691 and EP-A-0241947. It is preferred to reintroduce the condensed liquid into the bed separate from the recycle gas using the process described in our U.S. Pat. No. 5,541,270, the teaching of which is hereby incorporated into this specification.

When using the catalysts of the present invention under gas phase polymerisation conditions, the catalyst, or one or more of the components employed to form the catalyst can, for example, be introduced into the polymerisation reaction zone in liquid form, for example, as a solution in an inert liquid diluent. Thus, for example, the transition metal component, or the activator component, or both of these components can be dissolved or slurried in a liquid diluent and fed to the polymerisation zone. Under these circumstances it is preferred the liquid containing the component(s) is sprayed as fine droplets into the polymerisation zone. The droplet diameter is preferably within the range 1 to 1000 microns. EP-A-0593083, the teaching of which is hereby incorporated into this specification, discloses a process for introducing a polymerisation catalyst into a gas phase polymerisation. The methods disclosed in EP-A-0593083 can be suitably employed in the polymerisation process of the present invention if desired.

Although not usually required, upon completion of polymerisation or copolymerisation, or when it is desired to terminate polymerisation or copolymerisation or at least temporarily deactivate the catalyst or catalyst component of this invention, the catalyst can be contacted with water, alcohols, acetone, or other suitable catalyst deactivators a manner known to persons of skill in the art.

Homopolymerisation of ethylene with the catalysts of the invention may produce so-called "high density" grades of polyethylene. These polymers have relatively high stiffness and are useful for making articles where inherent rigidity is required. Copolymerisation of ethylene with higher 1-olefins (eg butene, hexene or octene) can provide a wide variety of copolymers differing in density and in other important physical properties. Particularly important copolymers made by copolymerising ethylene with higher 1-olefins with the catalysts of the invention are the copolymers having a density in the range of 0.91 to 0.93. These copolymers which are generally referred to in the art as linear low density polyethylene, are in many respects similar to the so called low density polyethylene produced by the high pressure free radical catalysed polymerisation of ethylene. Such polymers and copolymers are used extensively in the manufacture of flexible blown film.

Propylene polymers produced by the process of the invention include propylene homopolymer and copolymers of propylene with less than 50 mole % ethylene or other alpha-olefin such as butene-1, pentene-1, 4-methylpentene-1, or hexene-1, or mixtures thereof. Propylene polymers also may include copolymers of propylene with minor amounts of a copolymerizable monomer. Typically, most useful are normally-solid polymers of propylene containing polypropylene crystallinity, random copolymers of propylene with up to about 10 wt. % ethylene, and impact copolymers containing up to about 20 wt. % ethylene or other alpha-olefin. Polypropylene homopolymers may contain a small amount (typically below 2 wt. %) of other monomers to the extent the properties of the homopolymer are not affected significantly.

Propylene polymers may be produced which are normally solid, predominantly isotactic, poly α-olefins. Levels of stereorandom by-products are sufficiently low so that useful products can be obtained without separation thereof. Typically, useful propylene homopolymers show polypropylene crystallinity and have isotactic indices above 90 and many times above 95. Copolymers typically will have lower isotactic indices, typically above 80–85.

Depending upon polymerisation conditions known in the art, propylene polymers with melt flow rates from below 1 to above 1000 may be produced in a reactor. For many applications, polypropylenes with a MFR from 2 to 100 are typical. Some uses such as for spunbonding may use a polymer with an MFR of 500 to 2000.

Peroxide compounds may be added to ethylene or propylene polymers. For ethylene based polymers, peroxides can be used to give cross-linking in the polymer. For the preparation of high MFR propylene polymers, peroxide compounds may be added during extrusion for controlled rheology to increase the melt flow rate of polymer. Peroxide acts to break long polymer chains and has the effect of both increasing MFR and narrowing the molecular weight distribution (Mw/Mn) or polydispersity. A typical reactor polypropylene powder with an MFR of 2 g/10 min. by controlled rheology treatment with peroxide in an extruder may form a polymer with an MFR of 20–40. By varying the type, amount of, and process conditions using, peroxide, the final polymer MFR may be controlled as known in the art.

Depending upon the use of the polymer product, minor amounts of additives are typically incorporated into the polymer formulation such as acid scavengers, antioxidants, stabilizers, and the like. Generally, these additives are incorporated at levels of about 25 to 2000 ppm, typically from about 50 to about 1000 ppm, and more typically 400 to 1000 ppm, based on the polymer.

In use, polymers or copolymers made according to the invention in the form of a powder are conventionally compounded into pellets. Examples of uses for polymer compositions made according to the invention include use to form fibres, extruded films, tapes, spunbonded webs, moulded or thermoformed products, and the like. The polymers may be blown into films, or may be used for making a variety of moulded or extruded articles such as pipes, and containers such as bottles or drums. Specific additive packages for each application may be selected as known in the art. Examples of supplemental additives include slip agents, anti-blocks, anti-stats, mould release agents, primary and secondary anti-oxidants, clarifiers, nucleants, uv stabilizers, and the like. Classes of additives are well known in the art and include phosphite antioxidants, hydroxylamine (such as N,N-dialkyl hydroxylamine) and amine oxide (such as dialkyl methyl amine oxide) antioxidants, hindered amine light (uv) stabilizers, phenolic stabilizers, benzofuranone stabilizers, and the like. Various olefin polymer additives are described in U.S. Pat. Nos. 4,318,845, 4,325,863, 4,590,231, 4,668,721, 4,876,300, 5,175,312, 5,276,076, 5,326,802, 5,344,860, 5,596,033, and 5,625,090.

Fillers such as silica, glass fibers, talc, and the like, nucleating agents, and colourants also may be added to the polymer compositions as known by the art.

The present invention is illustrated in the following Examples and Comparative Examples.

EXAMPLES

Example 1

1.1—Preparation of 2,6-diacetylpyridinebis(2,6-dimethyl-4-tert.-butylanil)

To a solution of 2,6-diacetylpyridine (0.82 g; 5.01 mmol) in toluene (100 ml) was added 2,6-dimethyl-4-tert.-butylaniline (2.22 g; 2.5 eq.). After the addition of toluene sulphonic acid-monohydrate (0.05 g) the solution was refluxed overnight through a Dean-Stark apparatus. Upon cooling to room temperature the volatile components of the reaction mixture were removed in vacuo and the product crystallised from methanol. The product was filtered, washed with cold methanol and dried in a vacuum oven (50° C.) overnight. The yield was 1.96 g (81%).

1.2—Preparation of 2,6-diacetylpyridinebis(2,6-dimethyl-4-tert.-butylanil)$FeCl_2$.

$FeCl_2$ (0.45 g; 3.53 mmol) was dissolved in hot n-butanol (100 ml) at 80° C. and the 2,6-diacetylpyridinebis(2,6-dimethyl-4-tert.-butylanil) (1.70 g; 3.53 mmol) added as a solid portion-wise. The reaction mixture turned blue. After stirring at 80° C. for 60 minutes the reaction was allowed to cool down to room temperature and stir for 16 hours. The resultant suspension was filtered and the blue precipitate washed with pentane (3×50 $cm^3$) and dried in vacuo. The yield was 1.95 g (91%).

Example 2

Comparative 2.1—Preparation of 2,6-diacetylpyridinebis(2,4,6-trimethylanil)

To a toluene (150 ml) solution of 2,6-diacetylpyridine (2 g; 12.3 mmol) in a single neck 250 $cm^3$ round bottom flask was added 2,4,6-dimethyl aniline (5.16 $cm^3$; 36.8 mmol). Toluene sulphonic acid-monohydrate (0.1 g) was added to the solution and the flask connected in series to a Dean-Stark apparatus and water cooled condenser. The reaction mixture was refluxed for 20 hours during which the produced water from the condensation reaction was collected in the Dean-Stark apparatus. Upon cooling to room temperature the volatile components of the reaction mixture were removed in vacuo and the product crystallised from methanol. The product was filtered, washed with cold methanol and dried in a vacuum oven (50° C.) overnight. NMR and IR revealed the product to be exclusively 2,6-diacetylpyridinebis(2,4,6-trimethylanil) The yield was 4.23 g (87%).

2.2—Preparation of 2,6-diacetylpyridinebis(2,4,6-trimethylanil)$FeCl_2$.

$FeCl_2$ (3.19 g; 25.2 mmol) was dissolved in hot n-butanol (400 ml) at 80° C. and the 2,6-diacetylpyridinebis(2,4,6-trimethylanil) (10.0 g; 25.2 mmol) added as a solid portion wise. The reaction mixture turned blue. After stirring at 80° C. for 60 minutes the reaction was allowed to cool down to room temperature and stir for 16 hours. The resultant suspension was filtered and the blue precipitate washed with toluene (2×200 $cm^3$) and pentane (1×100 $cm^3$) and dried in vacuo. The yield of 2,6-diacetylpyridinebis(2,4,6-trimethylanil)$FeCl_2$ was 12.87 g (97%).

Example 3

Preparation of a Supported Catalyst 3.1—Pre-impregnation of support with activator compound "ES70X" Silica (25 g, calcined at 250° C., 10 hours under flowing nitrogen) was placed in a 250 ml round bottomed flask and toluene added (50 ml). MAO was added to the silica at room temperature (62 ml, 1.78M MAO in toluene) and the flask heated to 80° C. for 1 hour with constant stirring. Drying of the support was at 80° under vacuum.

3.2—Catalyst supporting/activation

To a toluene (20 ml) slurry of the silica/MAO (2.5 g) prepared as described in Example 3.1, solid 2,6-diacetylpyridinebis(2,6-dimethyl-4-tert.-butylanil)FeCl$_2$ (0.040 g) (prepared as described in Example 1.2) was added at room temperature. The mixture was occasionally shaken over a 1 hour period. The supernatant solution was removed and the silica/MAO/Fe complex dried under vacuum at 25° C. Analysis of the catalyst gave 0.14%w/w Fe.

Example 4

Comparative—Supported Catalyst Preparation

The preparation of 2,6-diacetylpyridinebis(2,4,6-trimethylanil)FeCl$_2$ is described in Comparative Example 2. Silica (1.38 g ES70, supplied by Crosfield), which had been heated under flowing nitrogen at 700° C., was placed in a Schlenk tube and toluene (10 ml) was added. To a solution of 2,6-diacetylpyridinebis(2,4,6-trimethylanil)FeCl$_2$ (0.041 g) in toluene (10 ml) was added methylaluminoxane (13.2 ml, 1.78M in toluene, supplied by Witco). This mixture was heated at 40° C. for 30 minutes to dissolve as much of the iron complex as possible. The solution was then transferred to the silica/toluene. The silica/MAO/toluene mixture was maintained at 40° C., with regular stirring, for 30 minutes before the toluene was removed, at 40° C., under vacuum to yield a free flowing powder. Analysis of the solid gave 16.9%w/w Al and 0.144%w/w Fe.

Example 5

Comparative—Preparation of Supported Catalyst 5.1 Pre-impregnation of support with activator compound Silica (Crosfield grade ES70X) was heated under flowing nitrogen at 250° for 16 hours. A sample of this silica (2.5 g) was placed in a Schlenk tube and had 12.1 ml of 1.78M methylaluminoxane, MAO (supplied by Witco) added to it to form a slurry. The slurry was heated for 4 hours at 50° C. before being left for 10 days at room temperature. The supernatant liquid above the silica was removed and the silica/MAO washed three times with toluene (3×10 ml) at room temperature, removing the supernatant solution each time.

5.2—Supported Catalyst Preparation (2,6-diacetylpyridinebis(2,4,6 trimethyl anil) iron dichloride (0.101 g) was slurried in toluene (20 ml), at room temperature, and added to the silica/MAO. The mixture was occasionally shaken over a 1 hour period. The supernatant solution was removed and the silica/MAO/Fe complex was washed with toluene until the filtrate was colourless. The solid was dried under vacuum at 50° C.

Example 6

Comparative—Supported Catalyst Preparation

To 2.0 g of silica/MAO (2.5 g) prepared as described in Example 3.1 was added 2,6-diacetylpyridinebis(2,4,6 trim-ethyl anil) iron dichloride (0.0273 g, 5.2×10$^{-2}$ mmol). The dry powders were thoroughly mixed and toluene (5 ml) was added. The slurry was shaken for 30 minutes during which time it changed from dark blue to orange/brown. The solvent was then removed under vacuum at 80° C. until fluidisation of the powder had stopped to yield a free flowing tan powder. Analysis of the catalyst gave 0.14%w/w Fe.

GAS PHASE POLYMERISATION TESTS

Examples 7–10

The reagents used in the polymerisation tests were: hydrogen Grade 6.0 (supplied by Air Products): ethylene Grade 3.5 (supplied by Air Products): hexene (supplied by Aldrich) distilled over sodium/nitrogen: dried pentane (supplied by Aldrich): methylaluminium (2M in hexanes, supplied by Aldrich): and triisobutylaluminium (1M in hexanes, supplied by Aldrich). A 3 liter reactor was baked out under flowing nitrogen for at least 1 hour at 77–85° C. before powdered sodium chloride charge powder (300 g, predried under vacuum, 160° C., >4 hours) was added. The sodium chloride was used as a fluidisable/stirrable start-up charge powder for the gas phase polymerisation. Trimethyl aluminium (3 ml, 2 molar in hexanes) was added to the reactor and was boxed in nitrogen. The alkyl aluminium was allowed to scavenge for poisons in the reactor for between a half and 1 hour before being vented using 4×4 bar nitrogen purges. The gas phase composition to be used for the polymerisation was introduced into the reactor and preheated to 77° C. prior to injection of the catalyst composition. The catalyst (0.18–0.22 g) was injected under nitrogen and the temperature then adjusted to 80° C. The ratio of hexene and/or hydrogen to ethylene during the polymerisation was kept constant by monitoring the gas phase composition by mass spectrometer and adjusting the balance as required. The polymerisation tests were allowed to continue for between 1 to 2 hours before being terminated by purging the reactants from the reactor with nitrogen and reducing the temperature to <30° C. The produced polymer was washed with water to remove the sodium chloride, then with acidified methanol (50 ml HCl/2.5 liters methanol) and finally with water/ethanol (4:1 v/v). The polymer was dried under vacuum, at 40° C., for 16 hours. The polymerisation tests were carried out at a polymerisation temperature of 80° C. and at an ethylene pressure of 8 bars. The polymerisation conditions and catalyst activities are set out in the following Table.

| Example No. (note 1) | Catalyst Example No. | TMA (mmols) (note 2) | H$_2$ (bar) | hexene (bar) | time (min) | Activity (note 3) | Fe residue (ppm) |
|---|---|---|---|---|---|---|---|
| 7 | 3.2 | 0 | 0 | 0 | 100 | 1781 | 2.35 |
| 8 | 3.2 | 6 | 0.5 | 0.2 | 60 | 2285 | 3.06 |
| 9 (Comp) | 4 | 6 | 0.5 | 0.2 | 60 | 1054 | |
| 10 (Comp) | 5.2 | 0 | 0 | 0 | 60 | 270 | |

Notes on the Table:
1 "Comp" Denotes Comparative Example
2. $^\#$2M Solution of trimethylaluminium in toluene (supplied by Aldrich)
3. Activity is expressed as g/mmol$^{-1}$/h$^{-1}$/b$^{-1}$ Molecular weight data on the polymer product is set out in the Table below.

| Example | Catalyst | Mw | Mn | Mpeak | Polydispersity |
|---|---|---|---|---|---|
| 7 | 3.2 | 328000 | 30000 | 116000 | 11.1 |
| 8 | 3.2 | 48000 | 8200 | 19000 | 5.9 |
| 9 (Comp) | 4 | 77000 | 6000 | 21000 | 12.8 |
| 10 (Comp) | 5.2 | | | | |

Branching and unsaturation data on the polymer products produced using the catalyst of the present invention is set out in the table below.

| EX. | Catalyst | Butyl branches/ 1000C* | Saturated chain ends/ 1000C* | Vinyl Chain ends/ 1000C# | Di-substituted olefin/ 1000C# |
|---|---|---|---|---|---|
| 7 | 3 | — | 0.6 | 0.64 | 0.09 |
| 8 | 3 | 0.2 | 2.8 | 0.74 | 0.08 |

Notes on the Table
*Measured by (13C) NMR
Measured by (1H) NMR

SLURRY PHASE POLYMERISATION TESTS

Example 11

A 1 liter reactor was heated under flowing nitrogen for 1 hour at 90° C. before being cooled to 40° C. Triisobutyl aluminium (3 ml of 1M in hexanes) followed by isobutane (500 ml) was added to the reactor. The reactor was sealed and heated to 80° C. increasing the pressure to 13.9 bar. Ethylene was added to give 22.0 bar total pressure, the vessel sealed and then cooled to 78° C. The catalyst described in Example 3.2 (0.090 g, slurried in hexane) was injected into the reactor raising the pressure by 0.9 bar. The reactor pressure was controlled at 22.8 bar during the test (ethylene pressure estimated to be approximately 8.0 bar) and the temperature adjusted to 80° C. Polymerisation was allowed to continue for 60 minutes. 65.9 g of polymer was recovered. Analysis of the polymer by GPC indicated Mw and Mn to be 298000 and 34000 respectively (polydispersity=8.9). Activity=732 g/g/hr. Iron residue in the polymer was calculated as 1.9 ppm.

Example 12

Comparative

A 1 liter reactor was heated under flowing nitrogen for 1 hour at 80° C. before being cooled to 30° C. Triisobutyl aluminium (3 ml of 1M in hexanes) followed by isobutane (500 ml) was added to the reactor. The reactor was sealed and heated to 80° C. increasing the pressure to 13.9 bar. Ethylene was added to give 21.9 bar total pressure, the vessel sealed and then cooled to 78° C. The catalyst described in Comparative Example 6 (0.090 g, slurried in toluene) was injected into the reactor raising the pressure by 0.1 bar. The reactor pressure was controlled at 22.0 bar during the test (ethylene pressure estimated to be approximately 8.0 bar) and the temperature adjusted to 80° C. Polymerisation was allowed to continue for 60 minutes. 53.1 g of polymer was recovered. Analysis of the polymer by GPC indicated Mw and Mn to be 329000 and 28000 respectively (polydispersity=11.7). Activity=590 g/g/hr

HALO-SUBSTITUTED COMPLEXES

The Fe complexes (1b, 2b and 3b) were prepared by reacting the appropriate ligand (1a, 2a and 3a) with $FeCl_2$.

TABLE 1

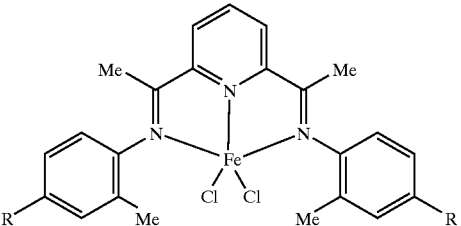

Complexes 1b, 2b, 3b
Substituents R on ligands 1a, 2a, 3a and complexes 1b, 2b and 3b

| R | Ligand | Complex |
|---|---|---|
| H | 1a | 1b |
| Me | 2a | 2b |
| F | 3a | 3b |

Example 13.1

Comparative

Preparation of 2,6-diacetylpyridinebis(2-methylanil) (1a)

To a solution of 2,6-diacetylpyridine (0.54 g, 3.31 mmol) in absolute ethanol (20 ml) was added 2-methylaniline (0.89 g, 8.3 mmol). After addition of a few drops of glacial acetic acid the solution was refluxed overnight. Upon cooling to room temperature the product crystallised from ethanol. The product was filtered, washed with cold ethanol and dried in a vacuum oven (50° C.) overnight. The yield was 0.42 g (33%). $^1$H NMR (250 MHz) ($CDCl_3$): δ 8.48 (d, 2H, Py-Hm), 7.91 (t, 1H, Py-Hp) 7.28 (m, 4H, ArH), 7.10 (m, 2H, ArH), 2.43 (s, 6H, N=$CCH_3$), 2.20 (s, 6H, $ArCH_3$).

Example 13.2

Comparative

Preparation of 2,6-diacetylpyridinebis(2,4-dimethylanil) (2a)

To a solution of 2,6-diacetylpyridine (0.54 g, 3.31 mmol) in absolute ethanol (20 ml) was added 2,4-dimethylaniline (1.0 g, 8.3 mmol). After addition of a few drops of glacial acetic acid the solution was refluxed overnight. Upon cooling to room temperature the product crystallised from ethanol. The product was filtered, washed with cold ethanol and dried in a vacuum oven (50° C.) overnight. The yield was 1.0 g (80%). $^1$H NMR (250 MHz) ($CDCl_3$): δ 8.42 (d, 2H, Py-Hm), 7.89 (t, 1H, Py-Hp) 7.05, (m, 4H, ArH), 6.62 (d, 2H, ArH), 2.37 (s, 6H, N=$CCH_3$), 2.36 (s, 6H, p-$CH_3$), 2.13 (s, 6H, o-$CH_3$).

Example 13.3

Preparation of 2,6-diacetylpyridinebis(2-methyl, 4-fluoroanil) ligand (3a)

To a solution of 2,6-diacetylpyridine (1.63 g, 0.01 mol) in absolute ethanol (25 ml) was added 2-methyl, 4-fluoroaniline (3.13 g, 0.025 mol). After addition of a few drops of glacial acetic acid the solution was refluxed for ten days. Volatiles were removed in vacuo and the compound obtained was washed with cold ethanol and dried in a vacuum oven (50° C.) overnight to give 1.9 g (50%) of 3a as a yellow solid. $^1$H NMR (250 MHz) ($C_6D_6$): δ 8.39 (d, 2H, $^3$J(HH) 7.8, Py-Hm), 7.24 (t, 1H, Py-Hp), 6.86–6.74 (m, 4H, Ar—H), 6.44–6.39 (m, 2H, Ar—H), 2.22 (s, 6H, N=CMe), 1.93 (s, 6H, Ar-Me); $^{19}$F NMR (235 MHz) (C$_6$D$_6$): δ −125.1 (s, 2F); EI mass spectrum, m/z 377 [M]$^+$.

Example 14.1

Comparative

Preparation of 2,6-diacetylpyridinebis(2-methylanil)FeCl$_2$ (1b)

A suspension of 1a (0.37 g, 1.08 mmol) in n-butanol was added dropwise at 80° C. to a solution of FeCl$_2$ (0.137 g, 1.08 mmol) in n-butanol (20 ml) to yield a blue solution. After stirring at 80° C. for 15 min. the reaction was allowed to cool to room temperature. The solvent was removed under vacuo and the solid obtained was washed with diethylether (3×10 ml), filtered and dried to afford 0.39 g (77%) of 1b as a blue powder. FAB+ mass spectrum, m/z 467 [M]$^+$, 432 [M-Cl]$^+$.

Example 14.2

Comparatives

Preparation of 2,6-diacetylpyridinebis(2,4-dimethylanil) FeCl$_2$ (2b)

A suspension of 2a (0.40 g, 1.08 mmol) in n-butanol was added dropwise at 80° C. to a solution of FeCl$_2$ (0.137 g, 1.08 mmol) in n-butanol (20 ml) to yield a blue solution. After stirring at 80° C. for 15 min. the reaction was allowed to cool to room temperature. The solvent was removed under vacuo and the solid obtained was washed with diethylether (3×10 ml), filtered and dried to afford 0.45 g (83%) of 2b as a blue powder. FAB+ mass spectrum, m/z 496 [M]$^+$, 461 [M-Cl]$^+$, 425 [M-2Cl]$^+$.

Example 14.3

Preparation of 2,6-diacetylpyridinebis(2-methyl, 4-fluoroanil) FeCl$_2$ (3b)

A suspension of 3a (0.590 g, 1.54 mmol) in n-butanol was added dropwise at 80° C. to a solution of FeCl$_2$ (0.195 g, 1.54 mmol) in n-butanol (20 ml) to yield a blue solution. After stirring at 80° C. for 15 min. the reaction was allowed to cool to room temperature. The solvent was removed under vacuo and the solid obtained was washed with diethylether (3×10 ml), filtered and dried to afford 0.69 g (87%) of 3b as a blue powder. FAB+ mass spectrum, m/z 503 [M]$^+$, 468 [M-Cl]$^+$.

Example 15

Oligomerisation of Ethylene

A liter reactor was baked out under a nitrogen flow for at least 1 hour at 85° C. The reactor was then cooled to 50° C. Isobutane (0.5 liter) and methylaluminoxane (0.8 ml of 10% weight solution in toluene supplied by Aldrich) were added and the reactor was boxed in nitrogen. The mixture was stirred for 30 min. Ethylene was introduced into the reactor until 5 bar over-pressure was achieved, then the premixed catalyst and co-catalyst solution in toluene was injected under nitrogen. The reactor pressure was maintained constant (5 bar ethylene over-pressure) throughout the polymerisation run by controlled addition of ethylene. The polymerisation reaction was performed at 50° C. for 1 hour. The reaction was quenched by addition of 3 ml of methanol and the reactor pressure vented. The reactor contents were then collected in 400 ml of toluene and washed with acidified water (50 ml). The organic phase (containing the soluble oligomers) was filtered (to recover low molecular weight polymer), dried over MgSO$_4$ and analysed by GC-MS technique. The low molecular weight (LM$_w$) polymer was dried in a vacuum oven (40° C.) overnight and analysed by GPC and NMR techniques.

Data from the oligomerisation tests are set out below in Tables 2, 3 and 4. Runs 1 and 2, which use the unsubstituted and methylated complexes respectively, are comparative examples.

TABLE 2

Oligomerisation tests

| Run | Pro-catalyst (μmol) | Co-catalyst ([Al]:[Fe]) | Ethylene Pressure (bar) | Yield of soluble fraction in toluene estimated by GC (g) | Yield of LM$_w$ (g) | Activity (g/mmol · h · bar) |
|---|---|---|---|---|---|---|
| 1 (comp) | 1b (6) | MAO 200:1 | 5 | 34.10 | 3.48 | 1253 |
| 2 (comp) | 2b (6) | MAO 200:1 | 5 | 25.43 | 5.86 | 1043 |
| 3 | 3b (3) | MAO 200:1 | 5 | 113.72 | 17.45 | 8745 |

TABLE 3

K factors for oligomer distribution

| Run | K |
|---|---|
| 1 | 0.792 |
| 2 | 0.777 |
| 3 | 0.797 |

TABLE 4

LM$_w$ polymer analyses

| Run | M$_w$ | M$_n$ | M$_w$/M$_n$ | Saturated Chain Ends (/1000 C) | Vinyl Chain Ends (/1000 C) | Me (/1000 C) | Et (/1000 C) | Bu (/1000 C) |
|---|---|---|---|---|---|---|---|---|
| 1 | 1500 | 700 | 2.1 | 16.2 | 13.1 | 0.7 | 1.0 | 0.7 |
| 2 | 1900 | 700 | 2.8 | 16.3 | 11.8 | 0.4 | 0.9 | 0.3 |
| 3 | 1300 | 650 | 2.0 | 22.9 | 18.1 | 0.8 | 1.4 | 1.1 |

These results show the substantially greater activity of the fluorinated complex compared with the methylated and unsubstituted equivalents.

What is claimed is:

1. A transition metal complex having the Formula (I)

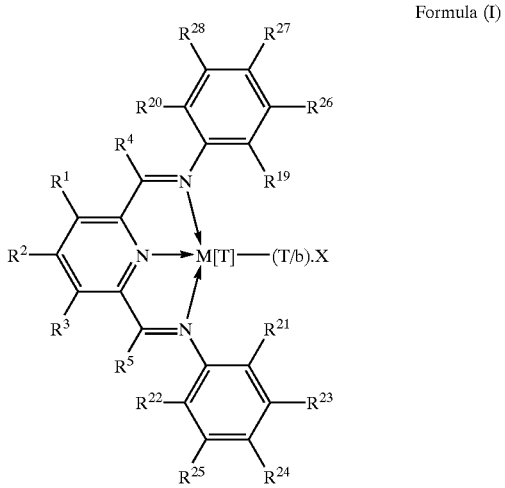

Formula (I)

wherein M is Fe[II], Fe[III], Co[I], Co[II], Co[III], Mn[I], Mn[II], Mn[III], Mn[IV], Ru[II], Ru[III] or Ru[IV]; X represents an atom or group covalently or ionically bonded to the transition metal M; T is the oxidation state of the transition metal M and b is the valency of the atom or group X; $R^1$, $R^2$, $R^3$, $R^4$, $R^5$, $R^{19}$, $R^{20}$, $R^{21}$, $R^{22}$, $R^{23}$, $R^{25}$, $R^{26}$ and $R^{28}$ are independently selected from the group consisting of hydrogen, halogen, hydrocarbyl, substituted hydrocarbyl, heterohydrocarbyl and substituted heterohydrocarbyl, wherein when any two or more of $R^1$, $R^2$, $R^3$, $R^4$, and $R^5$ are hydrocarbyl, substituted hydrocarbyl, heterohydrocarbyl or substituted heterohydrocarbyl, said two or more of $R^1$, $R^2$, $R^3$, $R^4$, and $R^5$ can be linked to form one or more cyclic substituents; and $R^{24}$ and $R^{27}$ are both halogen, both have two or more carbon atoms or one of $R^{24}$ and $R^{27}$ is halogen and the other of $R^{24}$ and $R^{27}$ has two or more carbon atoms.

2. The complex of claim 1, wherein $R^1$, $R^2$, $R^3$, $R^4$, $R^5$, $R^{19}$, $R^{20}$, $R^{21}$, $R^{22}$, $R^{23}$, $R^{25}$, $R^{26}$ and $R^{28}$ are independently selected from the group of hydrogen and $C_1$ to $C_8$ hydrocarbyl.

3. The complex of claim 2, wherein the $C_1$ to $C_8$ hydrocarbyl are methyl, ethyl, n-propyl, n-butyl, n-hexyl, n-octyl, phenyl or benzyl.

4. The complex of claim 1, wherein $R^{24}$ and $R^{27}$ are both halogen and are each independently selected from the group consisting of fluorine, chlorine, bromine and iodine.

5. The complex of claim 4, wherein $R^{24}$ and $R^{27}$ are both fluorine.

6. The complex of claim 1, wherein both of $R^{24}$ and $R^{27}$ have from 2 to 10 carbon atoms.

7. The complex of claim 6, wherein both of $R^{24}$ and $R^{27}$ have from 4 to 8 carbon atoms.

8. The complex of claim 1, wherein both of $R^{24}$ and $R^{27}$ have two or more carbon atoms and are each independently selected from the group consisting of ethyl, n-propyl, iso-propyl, n-butyl, sec-butyl, tert.-butyl, n-pentyl, neopentyl, n-hexyl, 4-methylpentyl, n-octyl, phenyl and benzyl.

9. The complex of claim 8, wherein both of $R^{24}$ and $R^{27}$ are tert.-butyl.

10. The complex of claim 1, wherein one of $R^{24}$ and $R^{27}$ has two or more carbon atoms and the other of $R^{24}$ and $R^{27}$ is halogen.

11. The complex of claim 10, wherein one of $R^{24}$ and $R^{27}$ is selected from the group consisting of ethyl, n-propyl, iso-propyl, n-butyl, sec-butyl, tert.-butyl, n-pentyl, neopentyl, n-hexyl, 4-methylpentyl, n-octyl, phenyl and benzyl and the other of $R^{24}$ and $R^{27}$ is selected from the group consisting of fluorine, chlorine, bromine and iodine.

12. The complex of claim 1, wherein $R^{19}$, $R^{20}$, $R^{21}$ and $R^{22}$ are each independently selected from the group consisting of methyl, ethyl, n-propyl, iso-propyl, n-butyl, sec-butyl, tert.-butyl, n-pentyl, neopentyl, n-hexyl, 4-methylpentyl, n-octyl, phenyl and benzyl.

13. The complex of claim 1, wherein one of $R^{19}$ and $R^{20}$ is hydrogen, one of $R^{21}$ and $R^{22}$ is hydrogen, and the other of $R^{19}$ and $R^{20}$ and $R^{21}$ and $R^{22}$ is each independently selected from the group consisting of methyl, ethyl, n-propyl, iso-propyl, n-butyl, sec-butyl, tert.-butyl, n-pentyl, neopentyl, n-hexyl, 4-methylpentyl, n-octyl, phenyl and benzyl.

14. The complex of claim 1, wherein the transition metal M is Fe(II), Fe(III) or Co(II).

15. The complex of claim 1, wherein X is selected from the group consisting of halide, sulphate, nitrate, thiolate, thiocarboxylate, $BF_4^-$, $PF_6^-$, hydride, hydrocarbyloxide, carboxylate, hydrocarbyl, substituted hydrocarbyl, heterohydrocarbyl, and β-diketonates.

16. The complex of claim 15, wherein X is selected from the group consisting of chloride, bromide, methyl, ethyl, propyl, butyl, octyl, decyl, phenyl, benzyl, methoxide, ethoxide, isopropoxide, tosylate, triflate, formate, acetate, phenoxide and benzoate.

17. The complex of claim 1, which is selected from the group consisting of 2,6-diacetylpyridinebis(2,6 dimethyl 4, t-butyl anil)FeCL$_2$, 2,6-diacetylpyridinebis(2,6 dimethyl 4, t-butyl anil)CoCl$_2$, 2,6-diacetylpyridinebis(2,6 dimethyl 4, t-butyl anil)FeBr$_2$, 2,6-diacetylpyridinebis(4, t-butyl anil)FeCl$_2$, 2,6-diacetylpyridinebis(2,6-dimethyl 4-phenyl anil)FeCl$_2$ and 2,6-diacetylpyridinebis(2-methyl, 4-fluoroanil)FeCl$_2$.

18. A polymerization catalyst comprising:
(a) a complex as defined in claim 1, and
(b) an activating quantity of at least one activator compound.

19. The catalyst of claim 18, wherein the activator is selected from the group consisting of organoaluminium compounds, hydrocarbylboron compounds and salts of a cationic oxidizing agent and a non-coordinating compatible anion.

20. The catalyst of claim 19, wherein the activator is selected from the group consisting of trimethylaluminium, triethyaluminium, tri-isobutylaluminium, tri-n-octylaluminium, methylaluminium, ethyaluminium dichloride, dimethylaluminium chloride, diethylaluminium chloride, ethylaluminiumsesquichloride, methylaluminiumsesquichloride, and alumoxanes.

21. The catalyst of claim 18, further comprising a neutral Lewis base.

22. The catalyst of claim 21, wherein the neutral Lewis base is selected from the group consisting of alkenes (other than 1-olefins), alkynes, primary amines, secondary amines, tertiary amines, amides, phosphoramides, phosphines, phosphites, ethers, thioethers, nitrites, esters, ketones, aldehydes, carbon monoxide, carbon dioxide, sulphoxides, sulphones and boroxines.

23. The catalyst of claim 18, which is supported on a support material selected from the group consisting of silica, alumina, MgCl$_2$, zirconia, polyethylene, polypropylene, polystyrene, and poly(aminostyrene).

24. A polymerization catalyst comprising:
(a) more than one complex as defined in claim 1, and
(b) an activating quantity of at least one activator compound.

25. A polymerization catalyst comprising:
(a) a complex as defined in claim 1,
(b) a tridentate nitrogen-containing Fe or Co complex, and
(c) an activating quantity of at least one activator compound.

26. The catalyst of claim 25, wherein (b) is 6-diacetylpyridine(2,4,6-trimethyl anil)$FeCl_2$.

27. A polymerization catalyst comprising:
(a) a complex as defined in claim 1, and
(b) a further catalyst for the polymerization of 1-olefins selected from the group consisting of a Ziegler-Natta catalyst system, a metallocene catalyst, a monocyclopentadienyl or constrained geometry catalyst and a heat activated supported chromium oxide catalyst.

28. A process for the polymerization or copolymerization of 1-olefins, comprising contacting a monomeric olefin or two or more monomeric olefins under polymerization conditions with a catalyst as defined in claim 18.

29. The process of claim 28 comprising the steps of:
(a) preparing a prepolymer-based catalyst by contacting one or more 1-olefins with the catalyst, and
(b) contacting the prepolymer-based catalyst with one or more 1-olefins.

30. The process of claim 28, wherein the polymerization is conducted in the presence of hydrogen as a molecular weight modifier.

31. The profess of claim 28 wherein the polymerization conditions are solution phase, slurry phase or gas phase.

32. The process of claim 31 wherein the polymerization is conducted under gas phase fluidized bed conditions.

33. The process of claim 31, wherein the polymerization is conducted in slurry phase in an autoclave or continuous loop reactor.

* * * * *

UNITED STATES PATENT AND TRADEMARK OFFICE
CERTIFICATE OF CORRECTION

PATENT NO.     : 6,461,994 B1
DATED          : October 8, 2002
INVENTOR(S)    : Vernon Charles Gibson et al.

It is certified that error appears in the above-identified patent and that said Letters Patent is hereby corrected as shown below:

<u>Column 20,</u>
Line 61, "nitrites" should read -- nitriles --.

Signed and Sealed this

Fifteenth Day of April, 2003

JAMES E. ROGAN
*Director of the United States Patent and Trademark Office*